United States Patent [19]
Kinlen et al.

[11] Patent Number: 4,908,117
[45] Date of Patent: Mar. 13, 1990

[54] SOLID STATE REFERENCE ELECTRODE

[75] Inventors: Patrick J. Kinlen, High Ridge; John E. Heider, Maryland Heights, both of Mo.

[73] Assignee: Monsanto Company, St. Louis, Mo.

[21] Appl. No.: 304,007

[22] Filed: Jan. 30, 1989

Related U.S. Application Data

[63] Continuation of Ser. No. 929,879, Nov. 13, 1986, abandoned.

[51] Int. Cl.⁴ .............................................. G01N 27/30
[52] U.S. Cl. .................................... 204/415; 204/435; 427/126.5; 427/409; 427/412.4
[58] Field of Search ............... 204/433, 435, 415, 416, 204/418; 427/409, 412.4, 123–125, 126.5

[56] References Cited

U.S. PATENT DOCUMENTS

| | | | |
|---|---|---|---|
| 4,115,209 | 9/1978 | Freiser et al. | 204/418 |
| 4,214,968 | 7/1980 | Battaglia et al. | 204/435 |
| 4,615,788 | 10/1986 | Seshimoto et al. | 427/125 |
| 4,818,365 | 4/1989 | Kinlen | 204/433 |

Primary Examiner—John F. Niebling
Assistant Examiner—Ben C. Hsing
Attorney, Agent, or Firm—Linda L. Lewis

[57] ABSTRACT

A solid state reference electrode comprising a metal/metal salt electrode, an immobilized electrolyte in contact with the metal salt, and a perfluorocarbon copolymer coating on the immobilized electrolyte to prevent migration of the electrolyte away from the electrode.

16 Claims, 1 Drawing Sheet

SOLID STATE REFERENCE ELECTRODE

This application is a continuation, of application Ser. No. 929,879, filed Nov. 13, 1986 abandoned.

FIELD OF THE INVENTION

This invention relates to a metal/metal salt solid state reference electrode wherein the electrode is in contact with an immobilized electrolyte. The immobilized electrolyte is coated with a perfluorocarbon copolymer cation exchange polymer. The reference electrode is used in combination with an indicator electrode as a pH sensor.

DESCRIPTION OF RELATED ART

There is a great variety of electrode types and structures for the measurement of various ions in solution. Typically, devices for obtaining such measurements include a reference electrode and a separate indicator electrode. When simultaneously immersed into a solution to be analyzed, the reference and indicator electrodes constitute an electrochemical cell across which a potential develops. This potential is proportional to the logarithm of the ionic activity which is related to ionic concentration, for example, hydrogen ion or pH. The foregoing relationship between the potential and ionic activity in solution is described by the well-known Nernst equation. An electrometric device, usually either a direct reading circuit or a null-balance potentiometric circuit is employed for measuring the potential between the electrodes.

A reference electrode typically comprises a glass electrode body for holding saturated potassium chloride (KCl) solution into which a $Hg/Hg_2Cl_2$ or $Ag/AgCl$ coated wire is dipped. The reference solution of the saturated KCl and a test solution is connected with each other across a porous fiber or plug. There is the possibility of the test solution mingling with the reference solution causing the reference electrode potential to change. In addition, the reference solution may leak out of the electrode contaminating the test solutions. Because of the requirement for a porous junction between reference solution and test solution, these electrodes are limited to test conditions of relatively low temperature and pressure.

U.S. Pat. No. 4,507,194 discloses a solid state reference electrode comprising a metal/metal salt electrode coated with a conductive substrate and a silver complex polymer. The silver complex polymer can be further coated with a film which prevents the penetration of obstructive ions. This reference electrode has a pH range limited to a pH of 9.0 or less.

U.S. Pat. No. 3,856,645 discloses a solid state reference electrode comprising a metal/metal salt electrode having a hydrophilic layer containing a soluble salt covered by a hydrophobic layer. The hydrophilic layer is usually polyvinyl alcohol which is applied by dipping the electrode in a solution of water, salt and polyvinyl alcohol. The hydrophobic layer consists of polymers such as polyvinyl chloride, which does not act as a cation exchange polymer.

U.S. Pat. No. 4,536,274 discloses a transcutaneous blood carbon dioxide sensor utilizing junction-type electrodes of palladium/palladium oxide and silver/silver halide electrodes applied to an electrically nonconductive substrate, partially coated with an insulated dielectric and partially coated with any of a number of polymeric membrane materials, including perfluorocarbon copolymer. This pH sensor is limited to measuring a narrow pH range of from 6.49 to 8.50, and is characterized by slow responsiveness and poor reproducibility.

U.S. Pat. No. 4,589,418 discloses a reference electrode of silver/silver chloride coated with a silicone base polymer containing saturated potassium chloride for measuring blood parameters such as pH and $PCO_2$.

Sekerka, I. and Lechner, J. F. in "Reference Electrode Base on Perfluorosulfonic Acid Membranes," Analytical Letts. 15(A7), 611 (1982) disclose reference electrodes utilizing cation exchange membranes such as perfluorocarbon copolymers. The electrodes disclosed are not solid state electrodes, but are two concentric plastic cylinders containing an internal electrolyte and an external electrolyte connected by a perfluorocarbon copolymer plug. These electrodes have the same disadvantages as the aqueous electrolyte reference electrodes discussed above.

DESCRIPTION OF THE INVENTION

The present invention involves a metal/metal salt solid state reference electrode and a method for making such electrode. The electrode comprises (a) an immobilized electrolyte in contact with the electrode, and (b) a coating of a perfluorocarbon copolymer cation exchange polymer on the immobilized electrolyte.

The metal/metal salt solid state reference electrode is made by the method comprising (a) contacting the metal/metal salt electrode with an immobilized electrolyte to coat the electrode, (b) drying the immobilized electrolyte, (c) contacting the immobilized electrolyte on the electrode with a a perfluorocarbon copolymer cation-exchange polymer to coat the immobilized electrolyte, (d) drying the coating on the electrode, (e) repeating (c) and (d) until the immobilized electrolyte is sufficiently coated, (f) curing the copolymer coating, (g) cooling the electrode, and (h) hydrating the copolymer coating.

DETAILED DESCRIPTION OF THE INVENTION

Figure 1:
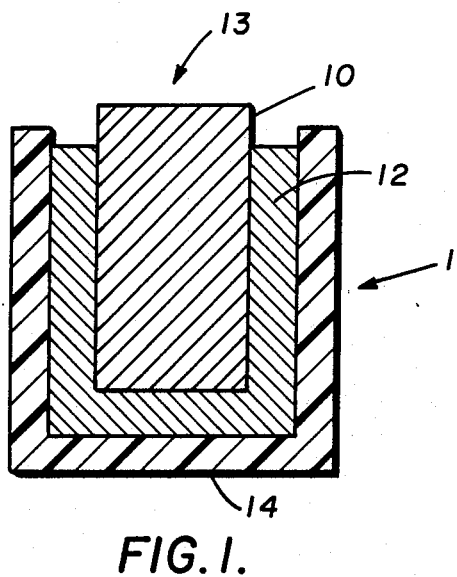
FIG. 1 is a cut away view of a solid state reference electrode made in accordance of this invention.

Referring to the drawings, FIG. 1 depicts a cut away view of a reference electrode (1) made in accordance with the present invention. The reference electrode (1) consists of a metal/me&.al salt electrode (10), and an immobilized electrolyte (12) wherein the immobilized electrolyte on the electrode is coated with a coating comprising cation exchange perfluorocarbon copolymer (14). The electode has a zone (13) for electrical contact.

In a preferred embodiment, a pH sensor is prepared wherein the present reference electrode is used in conjunction with the indicator electrode described in copending patent application Ser. No. 918,201, U.S. Pat. No. 4,818,365 which comprises solid state metal/metal oxide junction-type electrode coated with a perfluorocarbon copolymer cation exchange polymer, which is hereby incorporated by reference. Such an embodiment is shown in FIG. 2.

Figure 2:
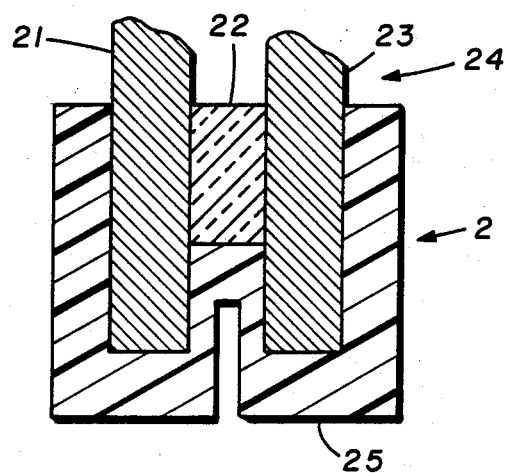
FIG. 2 is a cut away view of a pH sensor made in accordance of this invention.

Referring to FIG. 2, a cut away view of pH sensor (2), the indicator electrode (21) consists of a junction-type metal/metal oxide junction-type electrode in combination with the reference electrode (23) which consists of the metal/metal salt electrode in contact with the immobilized electrolyte of the present invention and the electrically nonconductive material (22). The electrically nonconductive material (22) consists of any material that is substantially electrically nonconductive, such as a ceramic, refractory, thermoplastic material, or a thermosetting resin.

The indicator electrode and reference electrode together in combination function as a pH sensor. The sensing portion of the electrodes is coated with a perfluorocarbon copolymer (25) described in detail hereinafter. The sensor has a zone (24) for electrical contact. The electrodes (21) and (23) together define an electrical potential between them when contacted with a solution or electrolyte having a particular pH. By measuring an electrical potential difference between the indicator electrode (21) and the reference electrode (23) at the zone (24) for electrical contact, as the probe is successively immersed in electrolytes of a different pH, a relationship between a voltage difference between electrodes (21) and (23) and the pH of a particular electrolyte in contact wi&.h the electrodes may be established.

Although the electrode of the embodiment shown in FIGS. 1 and 2 is elongated, shape is of no particular importance.

The metal/metal salt electrode (10) comprises a conductive layer of a metal in conducting contact with a layer of a salt of the metal. The conductive metal layer can comprise any suitable conductive metal as known to those skilled in the art. Particularly useful conductive metals are silver, nickel, and platinum. The salt layer in contact with the conductive layer can comprise substantially any insoluble salt of the metal of the conductive layer which establishes a fixed interfacial potential with the metal of the conductive layer. Such layers generally comprise a salt of the metal which is a product of the oxidation of the metal, as, for example, AgCl, $Hg_2Cl_2$, etc. A highly preferred embodiment of the present invention utilizes the well-known $Ag/Ag_nX$ (wherein X=S, Cl, Br or I, and n=1 or 2) interface to establish the potential of the reference electrode. Electrode elements of this type can be prepared using a number of well-known techniques which include, by way of example, dipping of silver as a wire, a foil or a supported thin layer into a solution of molten silver halide. Generally techniques for chemically converting metal to metal halide involve exposure or contact of the surface of the metal, for example silver, with a solution of a salt of the halide to be formed in the presence of an oxidant for a period and at a temperature sufficient to cause the desired conversion. Other useful techniques for preparing such electrodes are described in U.S. Pat. Nos. 3,591,482, 3,502,560 and 3,806,439. Although the teachings of these references are directed primarily to the preparation of wire electrodes, those skilled in the art can adapt such techniques to the manufacture of electrodes constructed on thin films of polymeric support apparatus. Alternatively, a discrete layer of silver halide may be coated over the silver layer as long as appropriate contact between the silver and halide is maintained.

The immobilized electrolyte (12) of the present invention provides free electrolytes in direct contact with the metal salt of the reference electrode to provide a constant potential. The electrolytes are prevented from migrating away from the metal salt by the ion-selective perfluorocarbon copolymer. The immobilized electrolyte comprises a polymer which is at least partially cationic, such as quaternary ammonium polymers. Suitable polymers for conversion into cationic polymers include halogenated polymers and amine polymers. What is meant by a halogenated polymer is any halogenated polymer wherein the halogen is susceptible to nucleophilic displacement by a tertiary amine, such as polyvinyl benzyl chloride or polyphosphonitrillic chloride. Other types of halogenated polymers include chloromethylated vinylaromatics and polyvinyl chlorides. Such halogenated polymers can be quaternized by any known method of quaternization with a tertiary amine, such as exposing to tertiary amine vapors or soaking in a tertiary amine solution. The quaternized polymer can then be contacted with the electrode. Alternatively, the halogenated polymer can be contacted with the electrode and then quaternized in situ by any of the above methods.

Conversely, amine polymers may be used, which can be quaternized using halogenated compounds to form quaternary amines. The amines must be such that they do not complex with the metal of the electrode. Tertiary amine polymers are suitable, such as p-dimethylaminomethyl polystyrene. The amine must be capable of nucleophilic displacement reaction with the halogenated compound.

The quaternized polymer must be of sufficient molecular weight to form a film or coating on the electrode, yet have a molecular weight low enough to be non-crystalline in character, typically in the range of 5,000 to 150,000 daltons. The polymer also is selected to form a film on the electrode such that the coating of the perfluorocarbon copolymer will adhere to the immobilized electrolyte film. Additionally, the polymer is selected to maximize the concentration of electrolyte in contact with the metal salt of the electrode to generate a measurable, stable potential. Insufficient electrolyte will result in interferences from contaminates in the polymer or drift in potential. The preferred halogenated polymer is polyvinylbenzyl chloride, which is a readily available commercial polymer and is easily quaternized.

The perfluorcarbon copolymer cation exchange polymers (14) act as a barrier to the migration and subsequent loss of the immobilized electrolytes. These polymers are a copolymer of at least two monomers with one monomer being selected from a group including vinyl fluoride, hexafluoropropylene, vinylidene fluoride, trifluoroethylene, chlorotrifluoroethylene, perfluoro(alkylvinyl ether), tetrafluoroethylene and mixtures thereof.

The second monomer is selected from a group of monomers containing an $SO_2F$ or COF group. Examples of such second monomers can be represented by the formula $CF_2=CFR_1SO_2F$ or $CF_2=CFR_1COF$. $R_1$ in the formula is a bifunctional perfluorinated radical having from 1 to 25 carbon atoms. A preferred monomer has from 1 to 8 carbon atoms. One requirement upon the formula is the presence of at least one fluorine atom on the carbon atom adjacent the $-SO_2$ or COF group. The $R_1$ formula portion can be of any suitable or conventional configuration, but it has been found preferably that the vinyl radical comonomer join the $R_1$ group through an ether linkage.

Typical sulfonyl or carbonyl fluoride containing monomers are set forth in U.S. Pat. Nos. 3,282,875; 3,041,317; 3,560,568; 3,718,627 and methods of preparation of intermediate perfluorocarbon copolymers are set forth in U.S. Pat. Nos. 3,041,317; 2,393,967; 2,559,752 and 2,593,583.

Such perfluorocarbon copolymers are commercially available from C. G. Processing, Inc. or E. I. duPont under the trademark Nafion ®, or from Dow under the trademark PFSA ®.

The electrode includes an area or zone (13) whereby electrical contact may be made between the electrode and sensing instrumentation. Typically, these contact areas are electrically insulated and water-proofed. Any suitable or conventional electrical device for measuring electrical output, or for comparing electrical output of the indicator electrode to a reference electrode may be used. Typically, a pH probe using the indicator electrode of the present invention would produce electrochemical potentials ranging from −1.00 volts to +1.00 volts depending on the pH of the particular electrolyte. An electrical sensing device used with the present invention must be capable of distinguishing small voltage changes in that range.

The reference electrodes of the present invention can be used in conjunction with any of a number of conventional indicator electrodes. Such indicator electrodes include glass pH electrodes, ion selective electrodes, immobilized enzyme electrodes and metal/metal oxide electrodes.

PREPARATION OF THE REFERENCE ELECTRODE

The method for preparing the reference electrode involves contacting a metal/metal salt electrode in an at least partially quaternized polymer containing an immobilized electrolyte, drying the immobilized electrolyte, contacting the electrode having the immobilized electrolyte coating with a perfluorocarbon copolymer cation exchange polymer to form a coating over the immobilized electrolyte, drying the polymer coating, curing the polymer coating, cooling and hydrating the coating. The coating with perfluorocarbon copolymer and drying steps can be repeated as required to produce a coating which acts as a barrier for migration of electrolytes away from the electrode.

The electrode can be contacted with the immobilized electrolyte by methods such as spraying, vacuum depositing or dipping. In a preferred embodiment, a film is made on the electrode by immersing into a solution of about 1 to 10 wt. % of an at least partially quaternized polymer dissolved or suspended in a solvent such as THF, 2-methoxy ethanol or hexafluoroisopropanol or a mixture of such solvents. The partially quaternized halogenated polymer can be prepared by any known method of quaternizing a halogenated polymer. In a preferred embodiment, polyvinylbenzyl chloride is dissolved in a polar solvent such as THF or hexafluoroisopropanol. An excess of a tertiary amine such as triethylamine is added and the solution refluxed for a period sufficient for at least partial quaternization to occur, in the range of about 30 to 90 minutes. The quaternized polymer is purified, washed and dried according to any conventional method, then dissolved in any of the polar solvents described above. The metal/metal salt electrode is coated with the solution or suspension. The electrode should be sufficiently coated that upon visual inspection a continuous film or coating is observed on the electrode.

The immobilized electrolyte is dried by evaporation at room temperature of the solvent. The drying process can be accelerated by heating the coated electrode to about 100° C. or less.

The immobilized electrolyte on the reference electrode is then coated with a perfluorocarbon copolymer. The immobilized electrolyte on the electrode can be contacted with the perfluorocarbon copolymer by methods such as spraying, vacuum depositing or dipping. The preferred method of coating is by dipping the electrode in a solution or suspension containing one or more perfluorocarbon copolymers sufficiently to coat the portion of the electrode in contact with the immobilized electrolyte. The concentration of the copolymer is sufficiently high to provide a thin film covering in a minimal number of coatings. In a preferred embodiment, an electrode is coated by dipping into a solution of about 5% to about 15% by weight of Nafion ® perfluorocarbon copolymer of 1100 equivalent weight in a low aliphatic alcohol and water. The electrode is then dried to remove the solvent, by means such as heating, air drying at room temperature, or drying in a desiccator. If heating to dry, the temperature should not be raised above about 120° C. so as not to disturb the molecular configuration of the polymer. The preferred means of drying is to air dry at room temperature for about 15 to 60 minutes. The coating procedure is repeated until the electrode is completely coated with a thin film sufficient to completely cover the electrode. The preferred number of coats is in the range of 1 to 5, the most preferred number of coats is 2 to 4.

The coated electrode is cured by heating or irradiating the electrode. When cured by heating, a temperature sufficient to allow a change in molecular configuration of the polymer which provides a barrier to the migration of electrolyte away from the electrode is suitable. Although the mechanism of the curing and migration prevention is not understood, it is thought that some type of annealing of the polymer occurs resulting in a better defined domain structure. The coating must be thoroughly dried before heating to cure, or the copolymer, upon rapid heating, will form a surface film which will trap vaporized solvent under it which upon further heating will rupture and fracture the coating. The preferred method of drying involves placing the coated electrode in a vacuum oven at room temperature, reducing the pressure to about 2 to 20 kPa vacuum, and holding at this temperature and pressure for about 30 to 90 minutes. The polymer is cured by increasing the oven temperature slowly to a maximum temperature of about 280° C. for a period of time sufficient to cure. If the copolymer is overheated, degradation of the copolymer occurs, along with possible degradation of the immobilized electrolyte. If the copolymer is not heated to a sufficient temperature for a sufficient time, the copolymer will not cure and migration of the electrolyte will occur. The preferred maximum temperature range is about 180° C. to 230° C. The preferred time for maintaining the maximum temperature is about 15 to 60 minutes. The electrode is cooled by any conventional means that allows slow cooling. The preferred method is by turning off the oven and allowing the electrode to cool slowly to room temperature in the oven over a period of about 30 to 90 minutes. If cooled too quickly, the electrode may not properly cure because rapid cooling may cause contraction and cracking of the polymer coating or cause the polymer to crystallize.

The electrode is hydrated by any appropriate means, such as soaking, heating, steaming or boiling in a liquid or vapor such as water, water solutions or buffer solutions. In a preferred embodiment, the electrode is heated in a boiling buffer solution. The most preferred method is to boil the electrode in a 0.1M solution of phosphate buffer, around pH 7, for about 15 to about 45 minutes. The electrode is to cool in the solution and is stored in the buffer solution. Once the electrode is hydrated, it should be kept hydrated by contacting it with a water source such as storing it immersed in water, buffer solution or other aqueous solutions. Other water sources include water-saturated air and steam.

The electrode can be examined for proper coating of the perfluorocarbon copolymer by testing for migration of the electrolyte away from the electrode. This can be done by placing the electrode in deionized water for several hours and then examining for the presence of electrolyte. For example, if the electrolyte is chloride, a drop of silver nitrate would indicate the presence of chloride by turning cloudy or formation of a precipitate.

The following examples are for illustrative purposes only and are not meant to limit the claimed invention in any manner.

EXAMPLES

The following reference electrodes were made according to the present invention.

EXAMPLE 1

The Quaternized Polymer

About 0.1 mole of polyvinylbenzylchloride purchased from Aldrich, 940 West St. Paul Ave., Milwaukee, Wis. 53233 of molecular weight 50,000 to 100,000 daltons, was dissolved in THF with about 0.24 moles of triethyl amine and refluxed for one hour. A white polymeric material precipitated. The precipitate was washed and extracted with THF yielding a white polymeric crystalline substance which was soluble in 2-methoxyethanol, and formed a slurry in 1,1,1,3,3,3-hexafluoro-2-propanol, and insoluble in water. Infrared analysis indicated partial quaternization of the polymer. Elemental analysis of the polymer indicated about 33% quaternization.

Coating the Electrode

A silver/silver chloride electrode was immersed in a 4.0 weight % solution of the partially quaternized polymer in 2-methoxy ethanol. The electrode was withdrawn from the solution and allowed to air dry for about 30 min., then heated for about 30 min. at 100° C. The dry electrode was dip coated two times in a 10 wt % Nafion® 117, a perfluorocarbon copolymer of 1100 equivalent weight polymer, in a solution of lower aliphatic alcohols and water, available from C.G. Processing, Inc. The solution was purchased as a 5 wt. % solution and concentrated to 10 wt. % by evaporation. The electrode was air dried for about 30 min., between each coat. The electrode was placed in a room temperature oven at 5.5 kPa for about 30 min. The oven temperature was slowly brought up to 210° C. over a period of about 60 minutes. The electrode was heated at 210° C. for thirty minutes in the oven. The electrode was slowly cooled to room temperature over a period of about 1 hour by turning off the oven and leaving the electrode in it while cooling. The electrode was placed in a pH 7 phosphate buffer solution (0.1M) and heated to boiling and boiled for thirty minutes. The buffer solution containing the electrodes was removed from the heat and allowed to cool. The electrode was stored in the solution.

The electrode was tested for migration of electrolyte (chloride) from the electrode. It was heated in deionized water at 92° C. for about 2 hours. Silver nitrate solution was dropped into the water and no clouding or precipitation occurred.

The above electrode was used in combination with a glass electrode and upon titration from 1.5 pH to 12.4 pH was found to have an essentially linear, Nernstian response.

The above electrode was also used in combination with an titanium/iridium oxide junction-type electrode prepared as follows:

Junction-type, metal/metal oxide electrodes composed of $Ti/IrO_2$ were purchased from Englehard Corp., Specialty Metals Div., 700 Blair Rd., Carteret, N.J. 07008, and were prepared by iridium chloride decomposition on a titanium electrode.

The dry electrodes were dipped three times into 10 wt % Nafion® perfluorocarbon copolymer 117, of 1100 equivalent weight polymer in a mixture of lower aliphatic alcohols and water, available from C. G. Processing, Inc., and dried at 100° C. subsequent to each dipping. The solution was purchased as a 5 wt. percent solution and concentrated to 10 wt. percent by evaporation. The dried electrodes were placed in a room temperature oven and the oven temperature was slowly brought up to 210° C. over a period of about 45 minutes. The electrodes were cured by heated at 210° C. for thirty minutes in the oven. The electrodes were slowly cooled to room temperature over a period of about 1 hour by turning off the oven and leaving the electrodes in it while cooling. The electrodes were placed in a pH 7 phosphate buffer solution (0.1M) and heated to boiling and boiled for thrity minutes. The buffer solution containing the electrodes was removed from heat and allowed to cool. The electrodes were stored in the solution.

If the iridium oxide electrode was tested using cyclic voltammetry (CV) in the presence of ferrocyanide, the reversible CV for the reduction of ferricyanide to ferrocyanide would be effectively eliminated as an interference, e.g. migration of the $Fe(CN)_6^{-4}$ anion to the electrode would be prevented.

The junction-type electrode was used with the above reference electrode to measure pH. Upon titration from a pH of about 1.5 to about 12.4, an essentially linear Nernstian response was observed.

EXAMPLE 2

The Quaternized Polymer

About 0.1 mole of the polyvinylbenzylchloride described in Example 1 was dissolved in 100 ml methoxyethanol. About 0.5 moles of triethylamine was added and the solution heated at 60° C. for about an hour. The solution was stirred at ambient temperatures for 2 days. The polymer was precipitated by adding 100 ml of methoxyethanol and 200 ml THF. The precipitate was washed with THF and dried. The product was soluble in water, methoxy ethanol and methanol. Infrared analysis indicated complete quaternization of the polymer.

Coating the Electrode

The electrode was coated as described in Example 1 using a 2.5% solution of the quaternized polymer in methanol and tested as in Example 1 for migration of electrolyte (chloride) from the electrode. No migration was observed.

When used with a glass indicator electrode to measure pH, an essentially linear Nernstian response was observed. Likewise, when using a perfluorocarbon copolymer coated titanium/iridium oxide junction-type electrode (as described in Example 1) with the above reference electrode, an essentially linear, Nernstian response was observed.

Control

A dry silver/silver chloride electrode as described in Example 1 was immersed in a 4.5 weight % solution of 4-polyvinyl pyridine in methanol and allowed to air dry. The coating procedure was repeated three times. The coated electrode was soaked for about 5 min. in 0.5M HCl to protonate the pyridine to form pyridinium chloride salt. The electrode was air dried and dip coated with 5% Nafion ® 117 copolymer available from C. G. Processing, Inc. in methanol, air dried for about 30 min., then dried at 100° C. for about 30 min.

The coating with Nafion ® copolymer was repeated twice.

The response of the above electrode was measured versus a standard calomel electrode by immersing the electrode in various pH buffer solutions and measuring the millivolt response. The plot of pH vs millivolts was random and non-linear. It is possible that the pyridium chloride salt complexed with the silver of the electrode, causing a non-linear, non-Nernstian response.

I claim:

1. A metal/metal salt solid state reference electrode consisting essentially of
   (a) a metal/metal salt electrode comprising
      (1) a conductive layer of a metal, and
      (2) a layer of a salt of said metal in conducting contact with said conductive layer of said metal,
   (b) a coating of an immobilized electrolyte in contact with said metal salt layer, wherein said immobilized electrolyte coating contains the electrolyte of said metal salt, and
   (c) a coating of a cured perfluorocarbon copolymer cation exchange polymer on said immobilized electrolyte coating, wherein said polymer is cured by heating to a temperature sufficient to change the molecular configuration of said polymer so as to provide a barrier to migration of said electrolyte away from said electrode.

2. The solid state reference electrode of claim 1 wherein the metal/metal salt electrode is $Ag/Ag_nX$ where X is S, Cl, B or I and n=1 or 2.

3. The solid state reference electrode of claim 1 wherein the perfluorocarbon copolymer is a copolymer of at least two monomers wherein one monomer is selected from a group consisting of vinyl fluoride, hexafluoropropylene, vinylidene fluoride, trifluoroethylene, chlorotrifluoroethylene, perfluoro(alkylvinyl ether) and tetrafluoroethylene and the second monomer is selected from a group of monomers containing an $SO_2F$ or COF group.

4. The solid state reference electrode of claim 1 wherein the metal/metal salt electrode is Ag/AgCl.

5. The solid state reference electrode of claim 1 wherein the immobilized electrolyte comprises an at least partially quaternized halogenated polymer.

6. The solid state reference electrode of claim 1 wherein the immobilized electrolyte is an at least partially quaternized polyvinylbenzyl chloride.

7. A solid state reference electrode prepared by the method consisting essentially of
   (a) contacting a metal/metal salt electrode with a solution or suspension of an at least partially quaternized polymer containing immobilized electrolytes of the metal salt of said metal/metal salt electrode to form an immobilized electrolyte coating over said metal/metal salt electrode,
   (b) drying the electrode of step (a),
   (c) contacting the electrode of step (b) with a solution or suspension containing one or more perfluorocarbon polymer cation-exchange polymers to form a perfluorocarbon copolymer cation-exchange polymer coating over said immobilized electrolyte coating,
   (d) drying said perfluorocarbon copolymer cation-exchange polymer coating so as not to disturb the molecular configuration of said one or more perfluorocarbon copolymers cation-exchange polymers therein,
   (e) repeating steps (c) and (d) if the electrode of step (d) is not completely coated with a thin film of said one or more perfluorocarbon copolymer cation-exchange polymers until the electrode is sufficiently coated,
   (f) then curing the perfluorocarbon copolymer cation-exchange. polymer coating by heating to a temperature sufficient to change the molecular configuration of said one or more perfluorocarbon copolymer cation-exchange polymers so as to provide a barrier to migration of said electrolytes away from said reference electrode,
   (g) cooling the electrode of step (f), and
   (h) hydrating the electrode of step (g).

8. The solid state reference electrode of claim 7 wherein the metal/metal salt electrode is $Ag/Ag_nX$ where X is S, Cl, B or I and n=1 or 2.

9. The solid state reference electrode of claim 7 wherein the perfluorocarbon copolymer is a copolymer of at least two monomers wherein one monomer is selected from a group consisting of vinyl fluoride, hexafluoropropylene, vinylidene fluoride, trifluoroethylene, chlorotrifluoroethylene, perfluoro(alkylvinyl ether) and tetrafluoroethylene and the second monomer is selected from a group of monomers containing an $SO_2F$ or COF group.

10. The solid state reference electrode of claim 7 wherein the electrode is dip coated 2 to 5 times in about a 5% to 15% by weight solution of perfluorocarbon copolymer and air dried for about 15 to 60 minutes.

11. The solid state reference electrode of claim 10 wherein the electrode is cured by drying the electrode at about 2 to 20 kPa for about 30 to 90 minutes, heating in the range of about 180° C. to 230° C. for about 15 to 60 minutes and cooled to room temperature over a period of about 30 to 90 minutes.

12. The solid state reference electrode of claim 11 wherein the electrode of step (g) in step (h) is hydrated by boiling in a buffer solution for about 15 to about 45 minutes.

13. The solid state reference electrode of claim 7 wherein the immobilized electrolyte comprises an at least partially quaternized halogenated polymer.

14. The solid state reference electrode of claim 13 wherein the immobilized electrolyte is an at least partially quaternized polyvinylbenzyl chloride.

15. A method to make a solid state reference electrode consisting essentially of:
(a) dip coating a Ag/AgCl electrode in a solution or suspension of an at least partially quaternized polyvinylbenzyl chloride,
(b) drying the electrode,
(c) dipping the electrode in a solution or suspension containing about 5% to 15% by weight of a perfluorocarbon copolymer,
(d) drying the coated electrode at room temperature for about 15 to 60 minutes,
(e) repeating steps (c) and (d) if the electrode of step (d) is not completely coated with a thin film of said perfluorocarbon copolymer until the electrode is sufficiently coated with said perfluorocarbon copolymer,
(f) drying the electrode at about 2 to 20 kPa for about 30 to 90 minutes,
(g) heating the electrode in the range of about 180° C. to 230° C. for about 30 to 90 minutes to cure the copolymer coating, thereby changing the molecular configuration of said copolymer so as to provide a barrier to migration of the chloride of said partially quaternized polyvinylbenzyl chloride away from the electrode, and
(h) hydrating the electrode by boiling in a buffer solution for about 15 to about 45 minutes, wherein the perfluorocarbon copolymer is a copolymer of at least two monomers wherein one monomer is selected from a group consisting of vinyl fluoride, hexafluoropropylene, vinylidene fluoride, trifluoroethylene, chlorotrifluoroethylene, perfluoro(alkyvinyl ether) and tetrafluoroethylene and the second monomer is selected from a group of monomers containing an $SO_2F$ or $COF$ group.

16. The solid state reference electrode made according to the method of claim 15.

* * * * *